United States Patent [19]

Obel et al.

[11] Patent Number: 5,199,428
[45] Date of Patent: Apr. 6, 1993

[54] IMPLANTABLE ELECTRICAL NERVE STIMULATOR/PACEMAKER WITH ISCHEMIA FOR DECREASING CARDIAC WORKLOAD

[75] Inventors: Israel W. P. Obel, Johannesburg, South Africa; Ivan Bourgeois, Verviers, Belgium

[73] Assignee: Medtronic, Inc., Minneapolis, Minn.

[21] Appl. No.: 673,883

[22] Filed: Mar. 22, 1991

[51] Int. Cl.$^5$ ............................................... A61N 1/08
[52] U.S. Cl. .................................. 128/419 C; 128/703
[58] Field of Search ............ 128/703, 419 PG, 419 C, 128/420.5

[56] References Cited

U.S. PATENT DOCUMENTS

3,650,277 3/1972 Sjostrand et al. ................ 128/419 C
4,791,931 12/1988 Slate ................................ 128/419 PG Primary Examiner—Kyle L. Howell
Assistant Examiner—Scott M. Getzow
Attorney, Agent, or Firm—John A. Rissman; Harold R. Patton

[57] ABSTRACT

A method and apparatus for stimulating the right and/or left carotid sinus nerves or the right stellate ganglion or the epidural space at about $T_2$ with continuous and/or phasic electrical pulses in response to detected myocardial ischemia to decrease cardiac workload as a method to protect the myocardium. The automatic detection of the need for such stimulation is responsive to a change in ST segment variation different from a predetermined or programmed threshold suggesting acute myocardial ischemia and/or other criteria or indicators of myocardial ischemia, including changes if pH and/or oxygen saturation ($SO_2$) detected from a sensor located in the heart, preferably the coronary sinus. The system is implemented with a dual chamber pacemaker with programming and telemetry capabilities for automatically recording in memory the aforementioned values for periods of time preceding and following each instance of stimulation for telemetry out on command and for programming "on" one or more of the sensors.

32 Claims, 2 Drawing Sheets

IMPLANTABLE ELECTRICAL NERVE STIMULATOR/PACEMAKER WITH ISCHEMIA FOR DECREASING CARDIAC WORKLOAD

BACKGROUND OF THE INVENTION

1. Field of the Invention

This invention relates to a method and apparatus for electrically stimulating the certain nerves for the prevention or interruption of bouts of myocardial ischemia, either automatically or upon external command by the patient or physician.

2. Description of the Prior Art

Vagal stimulation for the treatment of supraventricular arrhythmias, angina pectoris, and heart failure with an automatic, permanently implantable, medical device has been reported in the literature at least as far back as the early 1960's. The paper "Vagal Tuning" by Bilgutay et al in the *Journal of Thoracic and Cardiovascular Surgery*, Vol. 56, No. 1, July, 1968, pp. 71-82, described the concepts of vagal stimulation in the treatment of supraventricular arrhythmias, angina pectoris, and heart failure employing an implantable vagal stimulator. Vagal stimulation was effected through the application of electrical stimulation to the vagus nerve by silastic coated, bipolar electrodes (of the type disclosed in Medtronic U.S. Pat. No. 3,421,511) surgically placed around the intact nerve or nerves. Bilgutay et al. designed and employed three different models of vagal stimulators, the first one having a magnetic switch by which it could be turned on or off from outside the body to study the effects of long term stimulation, the second type also implantable but powered from outside by induction using rf frequency, and the third, external type triggered by the R-wave of the subject's electrocardiogram to provide stimulation only upon an achievement of a certain heart rate. Bilgutay et al. found that when a pulsatile current with a frequency of ten pulses per second and 0.2 milliseconds pulse duration was applied to the vagus nerve, long term effective stimulation could be achieved, and also found that by increasing only the voltage amplitude and current, more predictable changes on the electrocardiogram could be obtained. The heart rate could be decreased down to half the resting rate while still preserving sinus rhythm with up to 9 volts applied voltage. Atrio-Ventricular (AV) conduction dissociation and third degree heart block resulted at amplitudes exceeding 9 volts, and complete asystole with vagal escape resulted when the applied voltage exceeded 20 volts. Low amplitude vagal stimulation was successfully employed to control induced tachycardias and ectopic beats, and the authors noted other advantages of vagal stimulation in alleviating adverse effects of available drug therapies.

Other investigators reported treatment of angina pectoris and paroxysmal atrio-ventricular junctional or supraventricular tachycardias through application of carotid sinus nerve stimulation employing the Medtronic Angistat carotid sinus nerve stimulator (csns) then available from Medtronic, Inc. in papers such as "Carotid Sinus Nerve Stimulation in the Treatment of Angina Pectoris and Supraventricular Tachycardia", *California Medicine*, 112:41-50, March, 1970, in papers reference therein. These papers describe the system for effecting carotid sinus nerve stimulation by a radio frequency responsive stimulator activated by the patient at will in response to the patient's awareness of the onset of angina and/or supraventricular tachycardia.

Angina pectoris is a chest pain that accompanies and is indicative of myocardial ischemia. Oftentimes myocardial ischemia is "silent" and not accompanied by angina pectoris, in either case, ischemia is an oxygen starvation of the myocardium that is a precursor to myocardial infarction or the death of the starved myocardial cells. To protect these cells, the cells' oxygen demand must be reduced (or coronary flow increased).

The oxygen demands of the heart are not simply a function of the external work of the heart, that is, the product of arterial pressure and cardiac output. The development by the ventricles of pressure (more strictly speaking, tension) has a high oxygen cost. In addition to tension, the level of myocardial contractility, that is the inotropic or contractual state of the myocardium, is a second important determinant of the heart's oxygen needs. A third factor, of course, is that the heart's oxygen consumption is a function of cardiac frequency—the number of times the heart contracts per unit of time. A number of other physiologic variables have been studied, but none even approach in importance the three factors mentioned above—tension, contractility and heart rate—in the determination of myocardial oxygen consumption.

It is generally appreciated that angina pectoris results from an imbalance between the heart's oxygen needs and the oxygen supply. In the large majority of patients this imbalance results from a defect in the delivery of oxygen to the myocardium as a consequence of obstruction in the coronary vascular bed secondary to atherosclerosis or coronary spasm. In other patients, however, this imbalance results to a significant extent from increased myocardial oxygen demands, as occurs in aortic stenosis, thyrotoxicosis and tachycardia. Ideal therapy for severe myocardial ischemia would be to restore the balance between supply and demand in as a physiologic a manner as possible—by increasing oxygen delivery when it is limited, and by reducing oxygen demands when these are excessive. In practice, it may be difficult or impossible to increase oxygen delivery, particularly in patients with diffuse severe atherosclerosis. Some researchers have sought to relieve angina pectoris by reducing myocardial oxygen consumption through stimulation of the vagus nerve.

Investigators focused upon the use of carotid sinus nerve stimulation in the treatment and control of angina pectoris for regulation of the patient's blood pressure, and observed that the effect of the application of carotid sinus nerve stimulation provided a safe means for initiating reflex vagal activity which in turn effected a slowing in a patient's heart rate or even terminating a supraventricular tachycardia.

In U.S. Pat. No. 3,650,277, it was also proposed to stimulate the left and right carotid sinus nerves in response to the detection of elevated mean arterial blood pressure to alleviate hypertension.

Thus it is well known that the application of stimulation to the right or left carotid sinus nerves, either directly or indirectly, has the effect of lowering blood pressure which in turn decreases ischemia and attendant angina pectoris symptoms, with the danger that an important brady-arrhythmia may be induced in the process.

Difficulties in detecting ischemia and providing proper amplitudes, frequencies and duration of the electrical stimulation has effectively led to the near abandonment of this therapy in recent years. It has also been shown that many important and significant episodes of ischemia may not be detected by the patient and further cardiac damage may follow. This limits the use of patient activator systems.

SUMMARY OF THE INVENTION

The present invention contemplates a method and apparatus for detecting ischemia and both affecting stimulation of nerves regulating blood pressure and heart rate to reduce the heart's oxygen requirements while providing pacing therapies to maintain the patient's heart rhythm within acceptable limits. It is thus an object of the present invention to ameliorate myocardial ischemia and maintain adequate cardiac rate through stimulation of the vagal nervous system (or other effective nerves) as well as the heart tissue in a concerted fashion dependent upon need as automatically determined by the system.

More particularly, the present invention contemplates the detection of an ischemic condition susceptible to correction by stimulation of such nerves by comparison of the patient's coronary sinus blood pH and/or oxygen saturation and/or electrocardiogram ST elevation to preset, normal thresholds and triggering burst stimulation of the nerves until the blood gas and/or ST segment variations have been returned to non-clinical risk levels.

Moreover, the method and apparatus of the present invention contemplates the inclusion of both atrial and ventricular sequential pacing in order to most physiologically overcome bradyarrhythmias and/or unphysiological AV delays induced by the nerve stimulation. The AV sequential demand pacemaker may be provided with memory capabilities of storing the patient's electrogram and blood gas signals for a predetermined time interval preceding and following each instance that nerve stimulation is found necessary for later telemetry out on command and analysis by the physician. The real time of the event may also be stored in memory for later telemetering out.

The system of the present invention is provided with sensors for detecting blood pH and oxygen saturation content ($SO_2$) and/or heart rate which are indicative of ischemia. Preferably the sensors are located in the coronary sinus or a coronary vein to measure the dissolved oxygen and/or the lactic acid level of myocardial venous return blood. The system preferably includes programmable thresholds against which the signals developed by the sensors and the ST elevation are compared.

In the practice of the invention, a physician may exercise a patient on a treadmill and thereby induce ischemia while measuring the QRS heart rate, ST segment thresholds, blood pH and blood gas values and program the threshold levels of those parameters and the operating characteristics or modes of the implantable device of the present invention.

At the same time, the physician may examine the efficiency of the vagal stimulation parameters in alleviating the patient's induced ischemia and attendant angina pain.

It is an object of the present invention therefore to provide an improved apparatus for influencing the blood pressure in a patient, in particular for reducing the blood pressure of a patient suffering from angina pectoris at appropriate times, by electrical stimulation of afferent nerve paths from the baroreceptors of the patient, in particular the carotid sinus nerve or nerves or the right stellate ganglion or the epidural space at about T2. The device according to the invention comprises an electrode or electrodes which can be applied on or close to such nerves or epidural space for stimulation thereof with short electric pulses and a pulse generator connected to said stimulator assembly for supplying the stimulating pulses thereto. Preferably one uses an electrode applied to each one of the carotid sinus nerves of the patient, in which case the pulse generator is provided with two pulse output trains generating circuits connected to said electrodes respectively. The device according to the invention is characterized in that it may further comprise a synchronization signal generator for producing a control signal for the pulse generator dependent on the heart activity of the patient, and that the pulse generator produces, in response to said control signal, a pulse train of limited length, which starts at the beginning of the heart cycle and in which the majority of pulses in the train are applied during the first portion of the heart cycle.

Thus, the present invention seeks to integrate the characteristics attendant to the onset of myocardial ischemia in order to treat the patient's myocardial ischemia and/or anginal symptoms by stimulation of the specified nerves and, where appropriate, the heart.

DESCRIPTION OF THE DRAWINGS

These and other advantages of the present invention are best understood with reference to the drawings, in which.

DETAILED DESCRIPTION OF THE PREFERRED EMBODIMENT OF THE INVENTION

Figure 1:
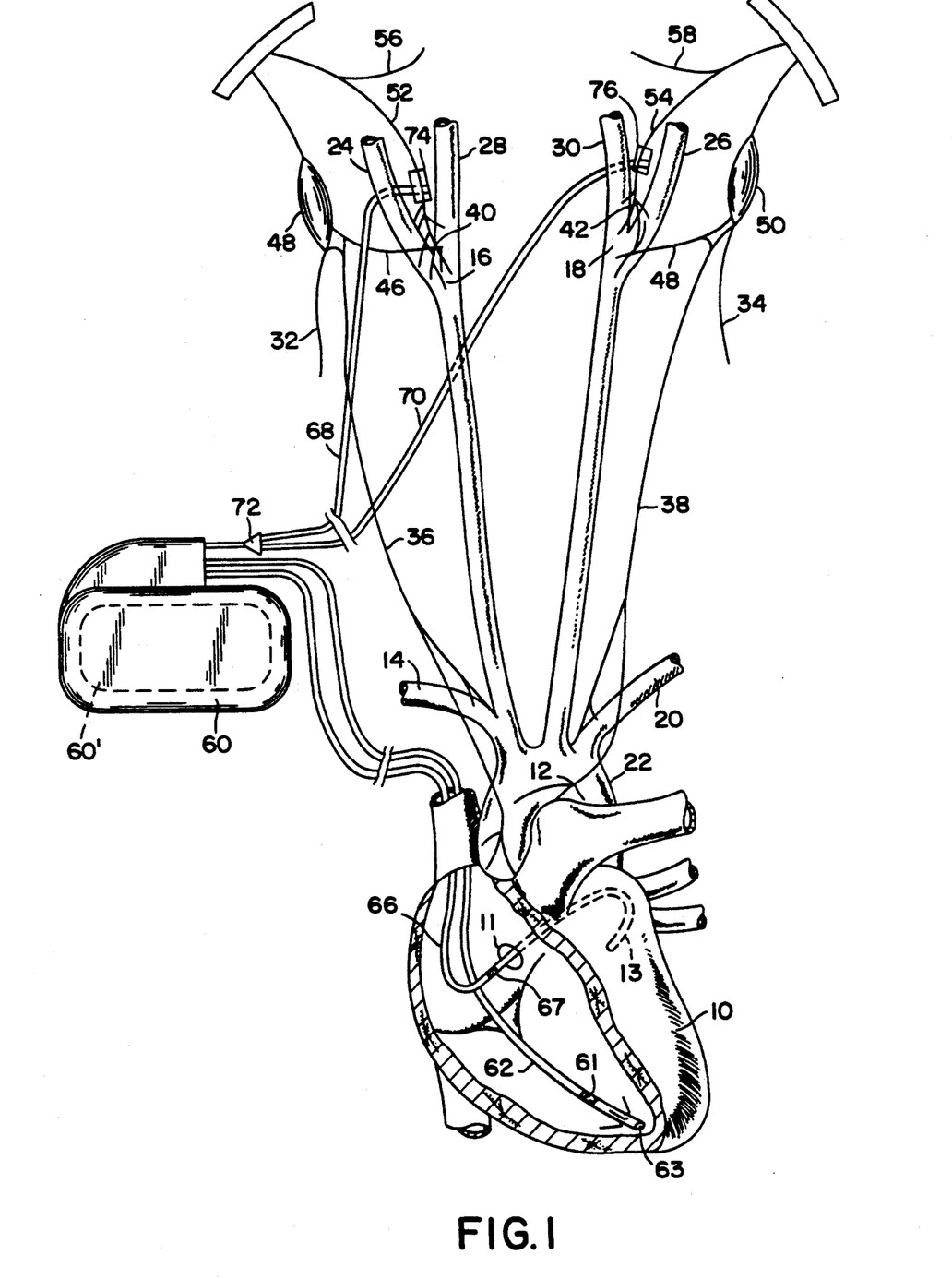
FIG. 1 is a diagrammatic illustration of the heart, its associated blood vessels and nerves, and the device of the present invention coupled thereto.

Before discussing the preferred embodiment of the present invention, it is helpful to briefly discuss the natural baroreceptor heart rate control system, which is shown in FIG. 1. The heart 10 pumps oxygenated blood out through the aortic arch 12, which leads to the right subclavian artery 14, the right common carotid 16, the left common carotid 18, the left subclavian artery 20, and the thoracic aorta 22. The body's system utilizes stretch receptors located in the arterial walls in the aortic arch 12 and at the bifurcation of the carotid arteries 16, 18 in the carotid sinus portion of the neck. The bifurcation of the carotid arteries 16, 18 leads to exterior carotid arteries 24, 26, respectively, and to interior carotid arteries 28, 30, respectively.

Nerve fibers extending from stretch receptors in the aortic arch 12 join the left and right vagus nerves 32, 34, respectively, with these fibers being referred to as cardiac depressor nerves 36, 38. A number of nerves extend from the stretch receptors at the bifurcation of the carotid arteries 16, 18 in the carotid sinus, with the areas immediately above the bifurcations being referred to as the carotid bodies 40, 42. Nerve branches 44, 46 extending from the carotid bodies 40, 42, respectively, join the ganglions of vagus 48, 50, respectively. Other nerve fibers comprising the sinus nerve branches 52, 54 (generally referred to as "Hering's nerves") of the glossopharyngeal nerves 56, 58, respectively, also extend from the carotid bodies 40, 42, respectively, to the medulla (not shown).

The rate of the heart is restrained by the right and left vagus nerves 32, 34, respectively in conjunction with the cardiac depressor nerves 36, 38, respectively. The cardio-inhibitory center of the nervous system exerts a tonic effect upon the heart, via the vagus nerves, restraining its rate. This effect is better known as vagal tone. The loss of vagal tone may be instrumental in triggering various arrhythmias including paroxysmal atrial tachycardias, premature atrial extra systoles, atrial fibrillation, tachycardia, etc. In either case, selective electrode stimulation of the right or left vagus nerve 32, 34 may, as shown by Bilgutay et al bring into control the tachycardias of ventricular or supraventricular nature without resorting to direct stimulation of the heart. With vagal stimulation, it is possible to slow the heart rate down and allow more complete cardiac relaxation.

It should be understood that for ease of illustration, the heart, the nerves, arteries, veins and pulse generator and lead system are not necessarily depicted in proper scale or proportion. In FIG. 1 the cutaway view of the heart 10 shows the coronary sinus opening 11 into the great coronary vein and associated lesser coronary veins into the right atrium. A pulse generator 60 having an indifferent case electrode 60' and containing the sensing, nerve stimulation and brady pacing pulse generators of the present invention is shown in relation to the heart 10 and the cardiac nerve system. A lead body 66 coupled to pulse generator 60 extends into the coronary sinus 11 and (optionally) deeply within the coronary vein 13 and preferably carries a pH and blood oxygen sensor (not shown in FIG. 1). A second lead 62 extends from the pulse generator 60 through the right atrium and into the right ventricle of the patient's heart to position an electrode 63 deep within the ventricular apex. The positioning of both the coronary sinus lead 66 and the right ventricular lead 62 in the heart is well known. Preferably the lead 66 carries at least one electrode 67 for providing sensing of the atrial electrogram and stimulation of the atrium. The electrode 67 may be located along lead body 66 to enable it to be positioned within the coronary sinus 11 or deeply within the coronary vein 13.

A second pair of electrical leads 68 and 70 extend from the connector block of the pulse generator 60 to respective nerve electrodes 74 and 76 placed around the right and left carotid sinus nerve bodies in a manner described, for example, in the aforementioned U.S. Pat. Nos. 3,421,511 and 3,522,811, both incorporated herein by reference.

The specific location of the nerve electrodes 74 and 76 may be varied, and it is contemplated that in the practice of the present invention it may be possible to place such electrodes at the right or left stellate ganglions (48 and 50). Alternatively, it is contemplated that a single lead and electrode could be extended from the pulse generator 60 to a dorsal column stimulating electrode. The electrode may be positioned in the epidural space roughly at level $T_2$ and may be of the type sold by Medtronic, Inc. as part of the Resume II ® and Picses-Sigma ® electrode system or described in Medtronic U.S. Pat. No. 4,414,986 and other Medtronic patents referenced therein.

In accordance with the present invention, it is contemplated that the lead 66 will carry a blood pH sensor of the type described in U.S. Pat. Nos. 4,009,721; 3,577,315; 3,658,053; 3,710,778. A membrane pH sensor electrode is typically placed in the right ventricle and senses pH, which is proportional to the blood concentration of carbon dioxide, which in turn is generated in increasing amounts by exercise as explained in U.S. Pat. No. 4,716,887. In the '721 patent, a diminution in the pH level is used to produce a higher paced cardiac rate. However, in the context of the present invention, it is contemplated that the pH sensor will be placed on lead 66 just inside the coronary sinus 11 to detect the level of lactic acid in venous return blood which is expected to increase with exercise of the cardiac muscle, particularly if the muscle is stressed by a lack of sufficient oxygen due to constriction in the cardiac arteries as a result of cardiac artery disease. Myocardial ischemia is virtually invariably associated with an increase in the blood lactic acid level in the coronary sinus. The increase in blood lactic acid level is accompanied by a decrease in pH.

In addition to the pH sensor, it is contemplated that the lead body 66 will also carry a dissolved blood oxygen sensor of the type described in Medtronic U.S. Pat. Nos. 4,750,495; 4,467,807 and 4,791,935, all incorporated herein by reference. An optical detector is used to measure the mixed venous oxygen saturation. In the aforementioned incorporated patents, a diminution in the mixed venous oxygen saturation is used to produce a higher paced cardiac rate.

In the context of the present invention, it is expected that the oxygen tension within the coronary sinus may be either increased or decreased during ischemia, although most times it would be decreased or remain the same. The reason for the increase would be that if a large area of the myocardium is ischemic and oxygen is not being supplied to that area, then the coronary sinus oxygen content might indeed increase. On the other hand, it would normally be expected that the oxygen content would decrease as dissolved oxygen decreases in those circumstances.

In the context of the present invention, it is expected that during the workup of the patient conducted by the physician, it would be determined whether or not the patient's heart condition would cause the change in oxygen saturation measured in the coronary sinus to be a meaningful predictor or indicator of ischemia or not. If not, then the system would be programmed to not employ the signal developed by the oxygen sensor or it would be in any case insufficient to trigger the detection of ischemia in a manner to be described hereafter. In either case, the system be configured to store the actual signal developed by the blood oxygen sensor in the event that the blood pH and/or ST segment variation satisfy the programmed ischemia thresholds for those sensors or values.

Turning to the ST segment variation detection, the pulse generator 60 is provided with a system for measuring the ST segment variation of the far field QRST complex measured between electrodes on leads 66 and 62. Myocardial ischemia is frequently associated with variation of ST segments of the QRST electrocardiogram measured both by surface EKG electrodes and by cardiac ECG electrodes. Again, the physician would determine and program into the implantable device 60 the ST variation threshold established in the workup of the patient during exercise and induced systems of angina pectoris.

Figure 2:
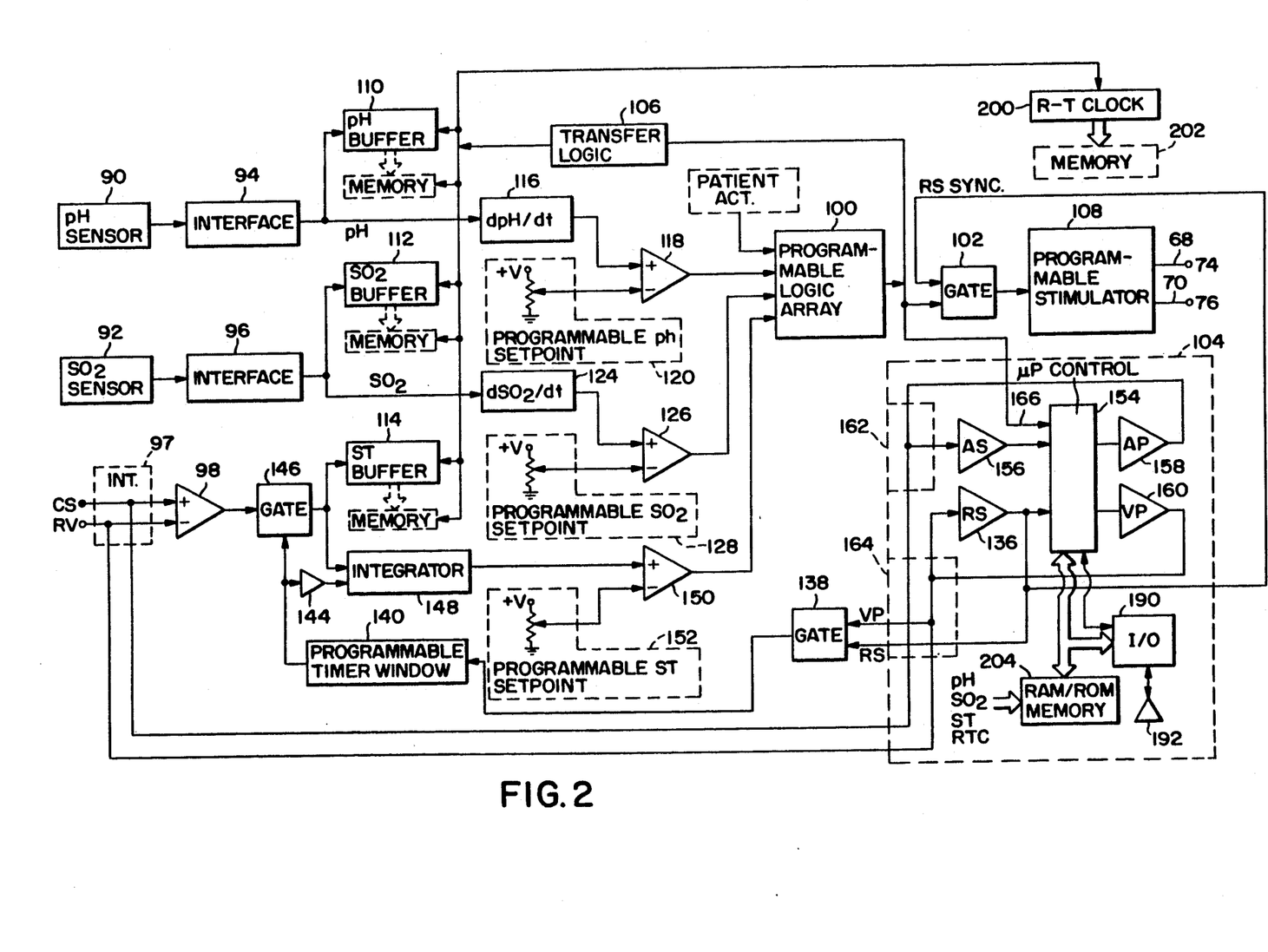
FIG. 2 is a block diagram of a system of the present invention for detecting ischemia, treating the ischemia and providing pacing therapies to the heart.

Turning now to FIG. 2, the overall system for detecting conditions of ischemia, stimulating the aforementioned nerves, providing backup brady and tachycardia pacing therapies and storing ischemic episodes is depicted. The system of FIG. 2 is preferably implemented in custom integrated circuit technology and may optionally be embodied in microprocessor architecture.

In FIG. 2, the pH sensor 90 and $SO_2$ sensor 92 develop output signals which are conducted by conductors within lead 66 to interfaces 94 and 96 which condition the signals as is well known in the art. The electrocardiogram ECG is measured between a coronary sinus electrode 67 and the right ventricular electrode 63 and applied through interface 97 to differential amplifier 98. The outputs of the interfaces 94 and 96 and the differential amplifier 98 are coupled through the signal processing circuits to the programmable logic array 100 in a fashion such that if one or more of the indicators of ischemia are present, the gate array 100 provides an output signal to a timing one shot 102, the DDD backup pacemaker 104 and the transfer logic block 106 so that the burst stimulator 108 is enabled to provide a burst of stimulating pulses to one or both electrodes 74 and 76 through respective leads 68 and 70, to effect transfer of data from the pH buffer 110, the $SO_2$ buffer 112 and the ST segment buffer 114 to permanent memory (not shown), and to switch on the DDD backup brady pacing.

Returning to the signal developed by the pH sensor 90 through interface 94, it is stored in pH buffer 110 and differentiated in differentiator 116 and thereafter applied to a first input terminal of the pH comparator 118 to determine whether or not the differentiated value of the blood pH falls below the rate of change of pH threshold, established by programmable set point 120, over a given period of time, e.g., 30 seconds. The output of the pH comparator is applied to one input of programmable array 100.

Similarly, the signal developed by the $SO_2$ sensor 92 processed by interface 96 is stored in $SO_2$ buffer 112, differentiated by differentiator 124 and applied to a first input terminal of the $SO_2$ comparator 126. The second input of the $SO_2$ comparator 126 is coupled to a programmable set point 128 for establishing a rate of change of $SO_2$ threshold. In the event that the differentiated $SO_2$ value falls above or below the set point 128, the output signal of comparator 126 is applied to a second input of logic array 100.

The measurement of the ST segment variation is somewhat more complicated in as much as it is necessary to provide a measurement window for the ST segment of the electrocardiogram which eliminates the possibility of inadvertently measuring the amplitude of the QRS complex itself. In order to accomplish this, it is contemplated that the QRS complex is sensed by a further sense amplifier 136 within the DDD pacemaker 104 having a first input terminal connected to the electrode 63 and a second input terminal connected to the case electrode 60 of the pulse generator 60 or to a further electrode on lead body 62 to develop an R-wave out signal RS each time the QRS complex occurs, in a manner well known in the pacing art. The signal RS is applied to one input of gate 138 which passes it to a timing window circuit 140. The gate 138 also receives at a second input terminal the ventricular stimulating pulse VP of the DDD backup pacemaker 104, in the event that it has been switched on either by the logic 100 or by the failure of the patient's heart to beat at the lower rate of the DDD pacemaker. In any event, the VP pulse is likewise passed through the gate 138 and can start the timing window circuit 140. The output of the circuit 140 provides the timing window commencing at the end of a delay after either a RS or VP signal and ending at the end of the programmed timing window. For example, the timing window may extend from 50 milliseconds following the production of either an RS or a VP signal and end 150 to 200 milliseconds thereafter. Within that time window, it would be expected that the electrocardiogram would exhibit the patient's ST segment so that its amplitude could be measured.

The output of the timing circuit 140 is applied to an inverter 144 and to gate circuit 146 for enabling the passage of the ST segment of the ECG signal to the input of the integrator 148. The integrator 148 integrates the voltage of the ST segment over the timing window and applies it to one input of the ST comparator 150. At the same time, the ST segment of the ECG is stored in ST buffer 114.

The second input of the ST comparator 150 is coupled to the programmable ST variation threshold set point 152. The output of the ST comparator 150 is coupled to the third input terminal of logic array 100. When the value of the integrated St segment exceeds the threshold, the ST comparator 150 provides a further signal indicative of the onset of ischemia to logic 100.

The programmable logic array 100, may be programmed from outside the patient's body by a programmer of the type described in Medtronic U.S. Pat. No. 4,550,370, incorporated herein by reference. Thus the physician can choose to use one or more of the output signals of the three sensors in combination. If more than one sensor is selected, then logic 100 operates as an AND gate requiring that all selected sensor outputs indicate the onset of ischemia before providing an output triggering signal to the DDD pacemaker 104, the one-shot 102 and the transfer logic 106.

When the conditions programmed into logic array 100 are satisfied it issues an output to one shot 102 which in turn issues a start command pulse to programmable stimulator 108. Programmed electrical stimulation pulse trains are applied to the electrodes 74, 76. If programmed "on," the pulse trains may be synchronized to the next detected RS out from amplifier 136.

Similarly, the external programmer can be used to control the setting of the thresholds of the programmable set points 120, 128 and 152 as well as the timing of the timing window circuit 140 and the synchronization delay of 108 to a ventricular event.

The DDD pacemaker depicted in block 104 also may include a discrete digital logic or microprocessor based timing and control circuit 154, an atrial sense amplifier 156 coupled to the coronary sinus electrode (or a separate atrial electrode bearing lead) for developing a P-wave out signal AS, and atrial and ventricular pulse generators 158 and 160 for producing the atrial and ventricular stimulating pulses AP and VP. The sense amplifiers and output pulse generators are coupled through blanking and refractory interfaces 97, 162 and 164 in a manner well known in the pacing art. The DDD pacemaker may have programmable parameters and modes as well as uplink and downlink telemetry as is well known in the art. The pacemaker may, for example, take the form of the Medtronic ® SYMBIOS ® Model 7005 or like pacemaker and the DDD pacemaker disclosed in Medtronic U.S. Pat. No. 4,390,020, both incorporated herein by reference. One specific operating mode for the pacemaker 104 may be to program it to operate only after receiving a trigger signal indicating ischemia at trigger input 166 and then only until the heart's own rate rises above a programmable lower rate.

Although a DDD pacemaker 104 is depicted, it will be understood that a single chamber pacemaker could also be used to stimulate only the ventricle and serve only the QRS complex. The pacemaker may take the form of any of the programmable pacemakers available in the prior art.

A further programmable feature of the system of the present invention lies in the selection of the burst pulse train stimulation frequency, amplitude and number of impulses in each burst as well as the spacing between impulses through the programmable stimulator 108. Again with the aid of an external programmer, the physician may select each of the parameters of the burst stimulation from an available menu at the time of patient workup. In addition, in this regard, the programmer may select one or both of the electrodes 74 and 76 for application of stimulation pulses to the desired nerves or the epidural space. The programmable implantable stimulator 108 may take the form of the Medtronic ® Itrel ® implantable neurological device Model 7424 programmed by the Model 7432 console programmer, both incorporated herein by reference.

In use of the system depicted in FIG. 2, it is contemplated that a patient would be selected for implantation of such a system by a workup procedure employing temporary pH and oxygen sensor bearing leads placed within the patient's coronary sinus and right ventricle coupled to an external version of the system depicted in FIG. 2 in order to ascertain the patient's thresholds at the onset of symptoms of angina pectoris. During this procedure the physician would select the parameters of the first stimulation from the menu (that would likewise be available in the implanted stimulator) and, from the effect on the heart rate settle on the initial therapies and sensing thresholds to be programmed in the implanted device.

A system depicted in FIG. 2 is contemplated to possess radio frequency telemetry 190, 192 for both the aforementioned downlink telemetry of programmable modes and parameters as well as uplink telemetry (as shown, for example, in U.S. Pat. No. 4,556,063) of data derived from the sensors and the electrocardiogram. To this end, the transfer-to-memory logic 106 effects the transfer of the contents of the buffers 110, 112 and 114 as well as the real time (date and time of day) clock 200 data into memory for later telemetry out of the pulse generator upon command. Such uplink telemetry systems are in current use in implantable pacemakers and other implantable medical devices.

The system depicted in FIG. 2 may advantageously also be combined with an anti-tachycardia pacing system where certain of the sensors may advantageously be employed to detect or confirm the detection of the supraventricular tachyarrhythmia. It will be understood that at times ischemia is accompanied by a supraventricular tachycardia and that the stimulation of the carotid sinus nerves or other nerves related thereto may effect both the lowering of the blood pressure as well as the heart rate and create AV block or prolongation. The DDD backup pacing in the system of the present invention is primarily intended to restore sequential heartbeat at the lower rate. However, the system may incorporate the anti-tachycardia pacing therapies in the event that the logic circuit 100 does not trigger the stimulator 108 because one or more of the sense conditions does not meet the ischemia threshold for that sensor.

The system may further include a patient-initiated storage of the aforementioned physiological conditions and treatment by delivery of stimulation. Failure of stimulation to prevent recurrences within a programmable period of time after detection of each episode is stored in memory and triggers an increase in stimulation amplitude and/or duration. Stimulation frequency may be varied in a predetermined manner from the optimum stimulation frequency, amplitude and duration determined during patient workup and a patient override may be provided to turn the stimulation on or off.

It will be apparent to those skilled in the art that the electronics of the system described above are easily attainable using available technology. The electronics may be embodied in custom integrated circuit and software based microprocessor technology. It will be understood that while the major components of the system, e.g. the pacemaker and nerve stimulator, have been referenced to existing discrete implantable devices, they and the remaining described components of FIG. 2 may all be incorporated within a single implantable device (with the elimination of duplicated features) and programmed by a single external programmer and telemetry receiver.

It will thus be appreciated that the present invention as described above defines a system having distinct advantages over previously existing systems for reducing ischemia by stimulation of nerves typically the carotid sinus nerves. This system features a high degree of specificity to ischemic conditions and a high degree of flexibility for recognizing and treating conditions and arrhythmias of a heart frequently associated with coronary artery disease and myocardial insufficiency.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications and alterations should therefore be seen within the scope of the present invention.

What is claimed is:

1. A system for influencing the natural biological blood pressure regulatory system in a patient, for reducing and controlling ischemia of myocardial tissue by electrical pulse by stimulation of the patient's nerve system, said system comprising:

ischemia sensor means adapted to be located within the venous return system of a patient's heart for sensing a constituent of the venous return blood draining from myocardial tissue and producing an electrical output signal substantially representing a chemical constituent of that blood;

signal transforming means for receiving the sensor means output signal and developing a stimulation trigger signal in response to an output signal indicative of a condition of ischemia; and means responsive to said trigger signal for applying electric stimulation pulses to said nerve system.

2. The system of claim 1 further comprising:

electrode means coupled to said patient's heart for detecting the patient's electrocardiogram;

means for responsive to said patient's electrocardiogram for developing a signal representative of the ST segment variation of that electrocardiogram;

means for comparing the measured ST segment variation to an ST segment variation threshold level and providing an ST segment output signal when the measured ST segment varies from the ST segment variation threshold in a predetermined manner; and means responsive to both said ST segment output signal and said trigger signal for triggering said stimulation means;

3. The systems of claim 1 or 2 wherein said ischemia sensor means further comprises:

a blood gas sensor means for detecting a value related to blood gas within the venous return system of said patient's heart and developing a blood gas signal in response to;

means for establishing a blood gas threshold value;

comparator means for comparing said blood gas signal to said blood gas threshold value and developing a blood gas difference signal;

and wherein said signal transforming means further comprises:

means for triggering said stimulating means in response to a predetermined value of said blood gas difference signal.

4. The system of claims 1 or 2 wherein said sensor means comprises means for detecting the pH of the patient's blood in the coronary sinus of the patient's heart.

5. The system of claims 1 or 2 wherein said sensor means comprises means for sensing dissolved blood oxygen ($SO_2$) in venous return blood in the coronary sinus region of said patient's heart.

6. The system according to claims 1 or 2 further comprising:

means for providing pacing stimulation energy pulses to said patient's heart in response to a low heart rate;

electrode means for coupling said pacing stimulation pulses to said patient's heart; and sensing means coupled to said electrode means for sensing the electrocardiogram of the patient's heart and determining that a bradycardia condition exists.

7. The system according to claim 1 further comprising:

means for storing values of said ischemia sensor means upon confirmation of ischemia; and means for telemetering said stored values to a remote location upon command.

8. The system according to claim 2 further comprising:

means for storing said measured ST segment signal; and means for telemetering said stored ST segment signal to a remote location on command.

9. A system for influencing the natural biological blood pressure regulatory system of a patient, for reducing and controlling ischemia of myocardial tissue by electrical pulse stimulation of the patient's nerve system, said system comprising:

electrode means coupled to said patient's heart for detecting the patient's electrocardiogram;

means for receiving said patient's electrocardiogram and developing a signal representative of the ST segment of that electrocardiogram;

means for providing an ST segment variation threshold value;

means for comparing the derived ST segment to said ST segment variation threshold level and providing an ST segment output signal when the measured ST segment variation varies from the ST segment variation threshold value in a predetermined manner; and means responsive to said ST segment output signal for applying electric stimulation pulses to said nerve system.

10. The system according to claim 9 further comprising:

means for providing pacing stimulation energy pulses to said patient's heart in response to a low heart rate;

electrode means for coupling said pacing stimulation pulses to said patient's heart; and sensing means coupled to said electrode means for sensing the electrocardiogram of the patient's heart and determining that a bradycardia condition exists.

11. The system according to claim 9 further comprising:

means for storing values of the ST segments upon confirmation of ischemia; and means for telemetering said stored values to a remote location on command.

12. A method of influencing the natural biological blood pressure regulatory system in a patient, for reducing and controlling ischemia of myocardial tissue by electrical pulse stimulation of the patient's nerve system, comprising the steps of:

sensing a constituent of the venous return blood draining from myocardial tissue and producing an output signal substantially representing a chemical constituent of that blood;

comparing said output signal to a set point threshold value and developing a stimulation trigger signal in response to a magnitude indicative of a condition of ischemia; and applying electric stimulation pulses to said nerve system in response to said trigger signal.

13. The method according to claim 12 further comprising the steps of:

detecting the patient's electrocardiogram;

receiving said patient's electrocardiogram and developing a signal representative of the ST segment variation of that electrocardiogram;

comparing the measured ST segment variation to an ST segment variation threshold level and providing an ST segment output signal when the measured ST segment variation varies from the ST segment variation threshold in a predetermined manner; and triggering a burst stimulator in response to said ST segment output signal.

14. The method according to claim 13 further comprising:

the step of detecting the level of a blood gas within the venous return system of said patient's heart and developing a blood gas signal in response to; and said comparing step further comprises:

establishing a blood gas threshold level, comparing said blood gas signal to said blood gas threshold level and developing a blood gas difference signal, and developing a trigger signal in response to a predetermined relationship between said blood gas signal and said blood gas threshold level, and said triggering step comprises triggering said burst stimulator in response to said ST segment output signal and said trigger signal.

15. The method according to claims 12 or 13 further comprising detecting the pH of the patient's blood in the coronary sinus of the patient's heart.

16. The method according to claims 12 or 13 further comprising the step of sensing dissolved blood oxygen ($SO_2$) in venous return blood in the coronary sinus region of said patient's heart.

17. The method according to claims 12 or 13 further comprising the steps of:
providing pacing stimulation energy pulses to said patient's heart in response to a low heart rate; and
sensing the electrocardiogram of the patient's heart and determining that a low heart rate condition exists.

18. A method of influencing the natural biological blood pressure regulatory system in a patient, for reducing and controlling ischemia of myocardial tissue by electrical pulse stimulation of the patient's nerve system said method comprising the steps of:
detecting said patient's electrocardiogram and developing a signal representative of the ST segment variation of that electrocardiogram;
comparing the derived ST segment variation to an ST segment variation threshold level and providing an ST segment output signal when the measured ST segment variation varies from the ST segment variation threshold in a predetermined manner; and
applying electric stimulation pulses to said nerve system in response to said ST segment output signal.

19. The method according to claim 18 further comprising:
providing pacing stimulation energy pulses to said patient's heart in response to a low heart rate; and
sensing the electrocardiogram of the patient's heart and determining that a low heart rate condition exists.

20. The method according to claim 18 or 19 further comprising the step of storing values of said ST segment variation upon confirmation of ischemia for telemetering out on command to a remote location.

21. A method of influencing the natural biological blood pressure regulatory system in a patient, for reducing and controlling ischemia of myocardial tissue by electrical pulse stimulation of the patients's nerve system, comprising the steps of:
continuously measuring the electrogram of the patient's heart;
detecting certain characteristics of said electrogram indicative of an ischemia condition of the myocardium;
initiating the storage of a sequence of said characteristics of said electrogram upon detection of an ischemic condition;
delivering one or more electrical stimulation therapies to the patient's nervous system for depressing the patient's heart rate; and
initiating the storage of a further sequence of said characteristics of said electrogram following delivery of said stimulation therapies.

22. The method of claim 21 further comprising the steps of:
examining the QRST segment of the patient's electrogram; measuring the ST segment variation of said QRST components of said electrogram;
comparing the measured ST segment variations to a threshold ST segment variation and providing a trigger signal when said measured ST segment variation differs from the threshold ST segment variation; and
delivering said stimulation therapies in response to said trigger signal.

23. A system for influencing the natural biological blood pressure regulatory system in a patient, for reducing and controlling ischemia of myocardial tissue by electrical pulse, stimulation of the patient's nerve system, said system comprising:
means for continuously measuring the electrogram of the patient's heart;
means for detecting certain characteristics of said electrogram indicative of an ischemic condition of the myocardriom;
means for initiating the storage of a sequence of said characteristics of said electrogram upon detection of an ischemic condition;
means for delivering one or more electrical stimulation therapies to the patient's nervous system for depressing the patient's heart rate; and
means for initiating the storage of a further sequence of said characteristics of said electrogram following delivery of said stimulation therapies.

24. The apparatus of claim 23 further comprising:
means for examining the QRST segment of the patient's electrogram;
means for measuring the ST segment variation of said QRST components of said electrogram;
means for comparing the measured ST segment variations to a threshold ST segment variation and providing a trigger signal when said ST segment variation differs from the threshold ST segment variation in a predetermined manner; and
means for delivering said stimulation therapies in response to said trigger signal.

25. A method of influencing the natural biological blood pressure regulatory system in a patient, for reducing and controlling ischemia of myocardial tissue by electrical pulse stimulation of the patient's nerve system, comprising the steps of:
sensing a constituent of the venous return blood draining from myocardial tissue and producing an output signal substantially representing a chemical constituent of that blood;
comparing said output signal to a set point threshold value and developing a stimulation trigger signal in response to a magnitude indicative of a condition of ischemia; and
applying electric stimulation pulses to said nerve system and storing said output signal in response to said trigger signal.

26. The method according to claim 25 further comprising detecting the pH of the patient's blood in the coronary sinus of the patient's heart.

27. The method according to claims 25 or 26 further comprising the step of sensing dissolved blood oxygen ($SO_2$) in venous return blood in the coronary sinus region of said patient's heart.

28. The method according to claim 25 further comprising the steps of:
detecting the patient's electrocardiogram and developing a signal representative of the ST segment variation of the electrocardiogram;
comparing the ST segment variation to an ST segment variation threshold level and providing an ST segment output signal when the detected ST segment variation differs from the ST segment variation threshold in a predetermined manner; and triggering a burst stimulator in response to both said ST segment output signal and said trigger signal.

29. A system for influencing the natural biological blood pressure regulatory system in a patient, for reducing and controlling ischemia of myocardial tissue by electrical pulse, stimulation of the patient's nerve system, said system comprising:

ischemia sensor means adapted to be located within the venous return system of a patient's heart for sensing a constituent of the venous return blood draining from myocardial tissue and producing an electrical output signal substantially representing chemical constituent of that blood;

signal transforming means for receiving the electrical output signal and developing a stimulation trigger signal in respond to said electrical output signal indicative of a condition of ischemia; and means responsive to said trigger signal for applying electric stimulation pulses to said nerve system and storing said output signal.

30. The system of claim 29 wherein said sensor means comprises means for detecting the pH of the patient's blood in the coronary sinus of the patient's heart.

31. The system of claims 29 or 30 wherein said sensor means comprises means for sensing dissolved blood oxygen ($SO_2$) in venous return blood in the coronary sinus region of said patient's heart.

32. The system of claim 29 further comprising:

electrode means coupled to said patient's heart for detecting the patient's electrocardiogram;

means for responsive to said patient's electrocardiogram for developing a signal representative of the ST segment variation of that electrocardiogram;

means for comparing the measured ST segment variation to an ST segment variation threshold level and providing an ST segment output signal when the measured ST segment variation differs from the ST segment variation threshold in a predetermined manner; and means responsive to both said ST segment output signal and said trigger for triggering said stimulation means;

* * * * *

UNITED STATES PATENT AND TRADEMARK OFFICE
CERTIFICATE OF CORRECTION

PATENT NO. : 5,199,428
DATED : April 6, 1993
INVENTOR(S) : Isreal W.P. Obel, et al It is certified that error appears in the above-indentified patent and that said Letters Patent is hereby corrected as shown below:

In the title item [54], on the title page, and column 1, line 3, add --DETECTOR-- after the word "ISCHEMIA".

Column 15, line 19 (claim 29), delete [respond] after the words "signal in" and add --response--.

Column 16, line 21 (claim 32), add --signal-- after the word "trigger".

Signed and Sealed this

Sixth Day of September, 1994

Attest:

BRUCE LEHMAN

*Attesting Officer*     *Commissioner of Patents and Trademarks*